United States Patent
Maeda et al.

(10) Patent No.: US 9,402,407 B2
(45) Date of Patent: Aug. 2, 2016

(54) METHOD FOR PREPARATION OF EUCALYPTUS EXTRACT

(75) Inventors: Yuuichi Maeda, Saitama (JP); Atsushi Narise, Saitama (JP); Sanae Kikuchi, Saitama (JP); Kenji Osawa, Saitama (JP)

(73) Assignee: LOTTE CO., LTD., Tokyo (JP)

( * ) Notice: Subject to any disclaimer, the term of this patent is extended or adjusted under 35 U.S.C. 154(b) by 13 days.

(21) Appl. No.: 12/999,896

(22) PCT Filed: Jun. 17, 2009

(86) PCT No.: PCT/JP2009/002760
§ 371 (c)(1),
(2), (4) Date: Feb. 2, 2011

(87) PCT Pub. No.: WO2009/153989
PCT Pub. Date: Dec. 23, 2009

(65) Prior Publication Data
US 2011/0129554 A1    Jun. 2, 2011

(30) Foreign Application Priority Data

Jun. 17, 2008  (JP) ................ 2008-157919

(51) Int. Cl.

| | |
|---|---|
| *A61K 36/61* | (2006.01) |
| *B01D 3/00* | (2006.01) |
| *C02F 1/02* | (2006.01) |
| *A23G 3/48* | (2006.01) |
| *A23G 3/34* | (2006.01) |
| *A23L 1/30* | (2006.01) |
| *A61K 36/14* | (2006.01) |

(52) U.S. Cl.
CPC .. *A23G 3/48* (2013.01); *A23G 3/34* (2013.01); *A23L 1/3002* (2013.01); *A61K 36/14* (2013.01); *A61K 36/61* (2013.01)

(58) Field of Classification Search
None
See application file for complete search history.

(56) References Cited

U.S. PATENT DOCUMENTS

| | | | | |
|---|---|---|---|---|
| 6,352,727 | B1 * | 3/2002 | Takahashi | 424/742 |
| 2006/0193962 | A1 * | 8/2006 | Kamiya et al. | 426/615 |
| 2009/0324754 | A1 * | 12/2009 | Fiorini-Puybaret et al. | 424/742 |

FOREIGN PATENT DOCUMENTS

| | | | |
|---|---|---|---|
| EP | 1062871 | A1 | 12/2000 |
| FR | 2904557 | A1 | 2/2008 |
| JP | 8109118 | | 4/1996 |
| JP | 8109118 | A * | 4/1996 |
| JP | 8259452 | | 10/1996 |
| JP | 8259452 | A * | 10/1996 |
| JP | 2001348307 | | 12/2001 |
| JP | 3365782 | | 1/2003 |
| JP | 2003159194 | | 6/2003 |
| JP | 2004065769 | | 3/2004 |
| JP | 200636672 | A * | 2/2006 |
| JP | 2006036672 | | 2/2006 |
| JP | 2000256345 | | 9/2009 |

OTHER PUBLICATIONS

Osawa et al. (1996) J. Nat. Prods. vol. 59, No. 9., 823-827.*
Nagata H. et al., Inhibitory Effects of Macrocarpals on The Biological Activity of Porphyromonas Gingivalis and Other Periodontopathic Bacteria, Oral Microbiol. Immnology Jun. 2006, vol. 21, No. 3, pp. 159-163.
Yusuke Shibuya, Hiroshi Kusuoku, Graham K. Murphy, and Yoshinori Nishizawa, Isolation and Structure Determination of New Macrocarpals from a Herbal Medicine, Eucalyptus globulus Leaf, Natural Medicines 55 (1), 28-31, 2001.
European Search Report Form EPO 1507S, Application No. 09766437.9-2114 / 2286678 PCT/JP2009002760, pp. 1-4, dated May 9, 2011.
Japanese Office Action, dated Sep. 25, 2013, pp. 1-4.

* cited by examiner

*Primary Examiner* — Chris R Tate
*Assistant Examiner* — Russell Fiebig
(74) *Attorney, Agent, or Firm* — Bond Schoeneck & King, PLLC; George McGuire; Blaine Bettinger

(57) ABSTRACT

A method for preparing a Eucalyptus extract which decreases the Eucalyptus-specific odor and obtains the effective ingredient in high purity and high yield as a physiologically-active ingredient. An essential oil constituent is removed from the Eucalyptus plant and the residue is extracted with water or an organic solvent aqueous solution. Next, the obtained extraction residue is further extracted with an organic solvent aqueous solution or an organic solvent, whereby Macrocarpal A, Macrocarpal B, and Macrocarpal C contained in the Eucalyptus as a physiological active substance are prepared in higher content than using conventional methods. Further, the extract has improved good taste, appearance, and other desirable properties.

5 Claims, No Drawings

METHOD FOR PREPARATION OF EUCALYPTUS EXTRACT

CROSS-REFERENCE TO RELATED APPLICATIONS

The present application is the United States national stage filing under 35 U.S.C. 371 of PCT Application Ser. No. PCT/JP2009/002760, filed on Jun. 17, 2009, which claims priority to JP Patent Application No. 2008-157919, filed on Jun. 17, 2008. The content of the above applications is relied upon and incorporated herein by reference in their entirety.

BACKGROUND OF THE INVENTION

1. Field of the Invention

The present invention relates to a method for preparing a Eucalyptus extract, and, more specifically, to method for preparing a Eucalyptus extract wherein an essential oil constituent is removed from a Eucalyptus plant, the residue is extracted with water or an organic solvent aqueous solution, and the obtained extract residue is further extracted with an organic solvent aqueous solution or an organic solvent, whereby macrocarpals in high yield are obtained.

2. Description of the Related Art

A Eucalyptus plant is a tall tree native to Australia and New Zealand and also cultivated in many parts of Japan. The essential oil obtained from the leaves (Eucalyptus oil) has a sensation of coolness and is used in medicine for a nasal catarrh and bronchial catarrh and also in an adhesive skin patch, dentifrice, insect deterrent, and the like. The plant is characterized by a very high growth rate and is therefore suitable for the substance production. Conventionally, new macrocarpals and method of preparation thereof is known, characterized in that an effective physiological active substance is isolated from the extract of Eucalyptus and the partial chemical structure is determined and named as macrocarpals and also obtained from a Eucalyptus plant (Japanese Patent Publication No. 3365782). Also, it is known that when extracting an effective to prevent and treat both of caries and periodontal disease, an essential oil component (Eucalyptus oil) is removed from a Eucalyptus plant, the residue is extracted with a polar solvent, the obtained extract and a phloroglucinol derivative contained in the extract have an extremely strong antibacterial activity against bacteria causing caries and periodontal disease as well as an inhibiting effect on collagenase produced by the periodontal disease causative bacteria *Porphyromonas gingivalis* (Japanese Patent Publication No. 2804232).

As thus described, the Eucalyptus extract has various kinds of effects such as an antibacterial effect and anti-inflammatory effect as well as a ceramide production promoting effect and quality improvement of hair. The Eucalyptus extract has a very unique and very strong odor that can be sensed even if the blending amount of the extract is very small. Therefore, when the extract is used for cosmetics, as a medical product, or as a quasi-drug and the like, various challenges were addressed to the problem that a sufficient amount to be effective could not be blended. For example, with regard to a method for producing a Eucalyptus extract, a producing method is known wherein a ratio of 1,8-cineole—which is known to be a Eucalyptus-specific odor causative substance—to Macrocarpal A is regulated to reduce the odor (Patent Publication No. 2006-036672). Another method is known wherein a color and an odor are removed from a solution of an extract prepared by extracting a Eucalyptus plant with a polar solvent by using an adsorbent (Patent Publication No. 2001-348307). On the other hand, a method for producing polyphenol compounds is known, wherein a Eucalyptus plant material is subjected to an extraction treatment with water at low temperature, thereafter the residue is subjected to a further extraction treatment with an aqueous alkaline solution, and the extract aqueous solution at low temperature mentioned in the above is treated with the addition of an adsorbent, thereafter the treatment solutions obtained from the extraction residues and the extract aqueous solution are then mixed together to obtain the active ingredient of the plant material in high yield (Patent Publication No. 2000-256345).

As thus described, various methods to prepare a Eucalyptus extract are known. However, to achieve a simplified step with a high concentration of macrocarpals as an effective ingredient in high yield is difficult, and also the obtained extract is unsatisfying with regard to taste, appearance, and other properties, as well as poor in versatility.

BRIEF SUMMARY OF THE INVENTION

It is therefore a principal object and advantage of the present invention to provide a new method for preparing a Eucalyptus extract with high yield and high purity.

It is another object and advantage of the present invention to provide a method for preparing a Eucalyptus extract that is suitable for food or beverage.

It is yet another object and advantage of the present invention to provide a method for preparing a Eucalyptus extract with decreased odor and flavor.

Other objects and advantages of the present invention will in part be obvious, and in part appear hereinafter.

In accordance with the foregoing objects and advantages, the present invention provides a method for preparing an extract from the Eucalyptus plant. The method comprises the steps of: (i) removing an essential oil constituent from the Eucalyptus plant; (ii) performing a first extraction step using a first solvent; and (iii) performing a second extraction step using a second solvent. In a preferred embodiment, the first solvent is a solvent solution comprising an organic solvent at a concentration of less than or equal to 30% by weight. In yet another embodiment, the second solvent is a solvent solution comprising an organic solvent at a concentration of greater than or equal to 30% by weight. The extract comprises Macrocarpal A, Macrocarpal B, and/or Macrocarpal C.

A second aspect of the present invention provides a method for preparing an extract from the Eucalyptus plant comprising the steps of: (i) removing an essential oil constituent from the Eucalyptus plant; (ii) performing a first extraction step using a first solvent; (iii) performing a second extraction step using a second solvent; and (iv) adding said extract to a food or beverage.

A third aspect of the present invention provides a food or beverage comprising an extract from a Eucalyptus plant, wherein the extract via a method comprising the following steps: (i) removing an essential oil constituent from the Eucalyptus plant; (ii) performing a first extraction step using a first solvent; and (iii) performing a second extraction step using a second solvent.

DETAILED DESCRIPTION OF THE INVENTION

It was found that high-yield macrocarpals could be obtained by removing an essential oil constituent from a Eucalyptus plant, extracting the residue with water or an organic solvent aqueous solution and further extracting the obtained extract residue with an organic solvent aqueous solution or an organic solvent; and the present invention has been completed.

The present invention enables Macrocarpal A, Macrocarpal B, and Macrocarpal C—which are physiological active substances included in the Eucalyptus—to be prepared in higher content than the conventional extracting method so that when it is used in product, the additive amount of the Eucalyptus extract can be decreased and the production rate can be improved. Also, components other than macrocarpals are reduced so that an extract having excellent taste, appearance, and other desirable properties can be prepared. Furthermore, the extracting method according to the present invention is only a solvent extraction process and therefore the use of a special separation purifying means such as a column and the like is not required. This also enabled the object to be prepared easily in high purity so that it has a great advantage in time and cost.

In the following, a preparation method of the present invention is explained in detail. Raw materials of a Eucalyptus plant used in the present invention are not limited in particular as far as it is a myrtaceous Eucalyptus plant, which can be used either alone or as a combination of two or more varieties. A part of a plant body to be extracted is not limited in particular, but the branches and leaves which can be collected easily are preferable. The leaves in particular are preferable. Also, the material could be either a fresh material, a dry form, or a mixture of both, and can be treated by a grinding down by friction and the like.

At first, a Eucalyptus plant, for example the leaves of the Eucalyptus, are pulverized by an appropriate pulverizing means such as a pulverizer and the like, preferably an essential oil constituent thereof is removed by using a steam distillation device that is generally used in an oil refining extraction. The removal of this essential oil constituent can be carried out by extracting by means of low polar solvents such as n-hexane, petroleum ether and the like at room temperature.

Water or the organic solvent aqueous solution as a first extraction solvent is applied to an essential oil extraction residue from which the essential oil is removed as above and the first extraction step is carried out. As the first extraction solvent, organic solvent used along with water includes but is not limited to, for example, petroleum ether, n-hexane, toluene, dichloroethane, chloroform, ether, ethyl acetate, acetone, methanol, ethanol, propanol, butanol, ethylene glycol, propylene glycol, butylene glycol and the like, preferably a lower alcohol having from one to five carbon atoms (methanol, ethanol, propanol, butanol, ethylene glycol, propylene glycol, butylene glycol and the like). The concentration of the organic solvent in the water or the organic solvent aqueous solution to be used is in a low concentration, not more than 30% by weight, preferably 0-20% by weight. Also, as for an extraction condition, an organic solvent aqueous solution of quantity of 2-100 times against the essential oil removed extraction residue can be immersed or heated to reflux at 20-100° C. for 10 minutes to 24 hours, and preferably it can be heated to reflux.

Next, the resulting product is subjected to a solid-liquid separation by means of a suction filtration or other means known in the art, the filtrate is removed, and the obtained extraction residue is further subjected to a second extraction step by using an organic solvent aqueous solution or an organic solvent as a second extraction solvent and the first extraction step is carried out. An organic solvent similar to the one used in the first extraction solvent can be used as the second extraction solvent. However, the concentration of the organic solvent aqueous solution or the organic solvent in the second step is over 30% by weight, preferably high concentration of 40-100% by weight, most preferably 50-80% by weight.

The extraction condition is equal to the condition used in the first extraction step, namely, an organic solvent aqueous solution or the organic solvent having an amount of 2-100 times to the amount of the first extraction residue can be immersed or heated to reflux at 20-100° C. for 10 minutes to 24 hours, although preferably it can be heated to reflux.

The obtained extraction solution is again subjected to solid-liquid separation by means of a suction filtration or other means known in the art, the organic solvent is removed and then freeze-dried, and thereby the desired extract is obtained. When the extraction temperature in two extraction processes falls below 20° C., macrocarpals cannot be extracted sufficiently and the yield is decreased so that it is not preferable. Similarly, when the concentration of the first extraction solvent is in a high concentration over 30% by weight, it is unfavorable since impurities other than the macrocarpals are produced. Further, when the concentration of the second extraction solvent is in a low concentration of not more than 30% by weight, it is unfavorable since the yield of the macrocarpals is decreased.

According to the above processes, the macrocarpals which is a physiological active substance can be obtained from Eucalyptus leaves in high yield. The examples of the obtained macrocarpals are listed in the following chemical structural formulas.

Chemical formula 1-Macrocarpal A

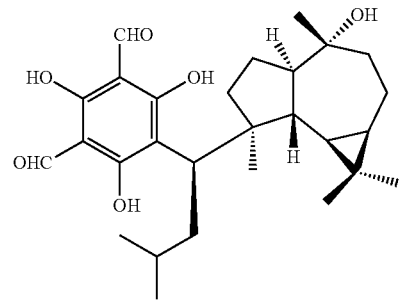

Chemical formula 2-Macrocarpal B

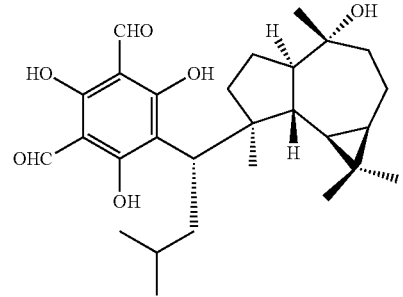

-continued

Chemical formula 3-Macrocarpal C

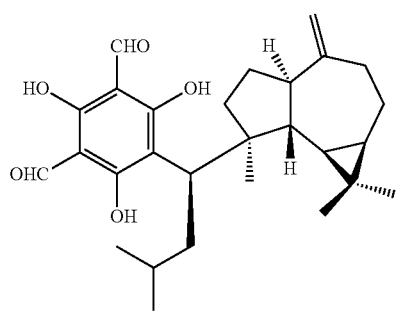

It is well known that the above mentioned Macrocarpal A, Macrocarpal B, and Macrocarpal C are effective to an antiviral action, HIV reverse-transcriptase inhibitory action and also to anti-tooth caries as well as a prevention of periodontal disease. By using the preparation method according to the present invention, Macrocarpal A, Macrocarpal B, and Macrocarpal C can provide about 3 to 5% by weight which is more than two times high in concentration compared to the conventional method, for example, the organic solvent extraction method wherein macrocarpals are extracted once with 60% by weight of ethanol.

The use of the extraction including an effective ingredient obtained in high yield by the preparation method of the present invention can be conceived variously, however, it possess a pleasing flavor, taste, and high safety and therefore it can be used in products in daily use, i.e. being blending in food and sanitary goods such as chewing gum, candy, tablet, gargle agent and tooth paste and the like. When the extract obtained in the present invention is blended in the food or sanitary goods, it is preferable to be added at the ratio of 0.001 to 10% by weight of the extract to the food or sanitary goods.

EXAMPLES

The comparative examples, examples, experimental examples, and application examples given below are intended to illustrate and not limit the scope of the claims herein.

Comparative Example 1

The essential oil of Eucalyptus leaves was removed by steam distillation, then the leaves were dried and pulverized, 100 ml of water or 10-100% by weight ethanol aqueous solution was added to 10 g of the resulting dried leave powder and then extracted under reflux at 60-90° C. for about 1 hour. The resulting extraction solution was filtrated and separated, the organic solvent of the extraction solution was removed and THEN freeze-dried, and thereby the desired extract was prepared. The extract was dissolved and quantitative analysis was conducted according to the following HPLC conditions:

I. Macrocarpal A, Macrocarpal B
Column: Cadenza CD-C18 (4.6×250 mm, 3 µm, Imtakt Corporation)
Mobile phase: A—Solution of 0.1% (v/v) trifluoroacetic acid in acetonitrile; B—0.1% (v/v) aqueous solution of trifluoroacetic acid, where A:B=75:25.
Flow rate: 1.0 ml/min
Column temperature: 40° C.
Detector: UV (275 nm)
Injection volume: 20 µl
II. Macrocarpal C
Mobile phase: A—Solution of 0.5% (v/v) acetic acid in methanol; B—0.5% (v/v) acetic acid aqueous solution, where A:B=88:12.
Other conditions are the same as I.

When extracting using the preparation method of this Comparative Example, the concentration of the organic solvent aqueous solution was varied in each sample. The comparative results of the macrocarpals content provided in Eucalyptus Extract Samples 1-9 are indicated in Table 1.

TABLE 1

| | Extraction Solvent | Macrocarpal Content in Extract (mg/g) | | |
| --- | --- | --- | --- | --- |
| | | Macrocarpal A | Macrocarpal B | Macrocarpal C |
| Extract 1 | Water | 0.000 | 0.000 | 0.000 |
| Extract 2 | 10% by weight of Ethanol Aqueous Solution | 0.023 | 0.000 | 0.000 |
| Extract 3 | 20% by weight of Ethanol Aqueous Solution | 0.510 | 0.380 | 0.000 |
| Extract 4 | 30% by weight of Ethanol Aqueous Solution | 2.882 | 2.436 | 2.008 |
| Extract 5 | 40% by weight of Ethanol Aqueous Solution | 7.130 | 5.490 | 4.329 |
| Extract 6 | 50% by weight of Ethanol Aqueous Solution | 7.231 | 5.189 | 6.883 |
| Extract 7 | 60% by weight of Ethanol Aqueous Solution | 6.600 | 5.270 | 10.111 |
| Extract 8 | 80% by weight of Ethanol Aqueous Solution | 6.750 | 5.400 | 12.655 |
| Extract 9 | 100% by weight of Ethanol | 8.420 | 6.640 | 15.430 |

Table 1 shows that even though the leaves of Eucalyptus are extracted with less than or equal to 30% by weight of ethanol concentration, most of Macrocarpal A, Macrocarpal B and Macrocarpal C remained in them.

Example 1

The essential oil of Eucalyptus leaves was removed by the steam distillation, then the leaves were dried and the dried leaves were pulverized, 100 ml of water or 30% by weight of ethanol aqueous solution (the first extraction solvent) was added to 10 g of the resulting dried leave powder and then extracted under reflux at 70-90° C. for about 1 hour. The resulting extraction solution was filtrated and separated, to the obtained extraction residue, 100 ml of 40-100% by weight of ethanol aqueous solution or ethanol (the second extraction solvent) was further added and then extracted under reflux at 70-90° C. for about 1 hour. The extraction solution was filtrated and separated, the organic solvent was removed and then freeze-dried and thereby the desired extract was prepared. The extract was dissolved and quantitative analysis was conducted according to the previous mentioned HPLC conditions.

When extracting using the preparation method according to this Example 1, the concentration of the organic solvent aqueous solution was varied in each sample. The comparative results of the macrocarpals contents provided in the Eucalyptus Extract Samples 10-18 are indicated in Table 2.

1. Preproduction Chewing Gum
Xylitol: 45% by weight
Maltitol: 33% by weight
Gum base: 14% by weight
Flavor material: 1% by weight
Each extract: 0.2% by weight
Others: remaining amount
Sum: 100% by weight 2. Preproduction Candy
Sugar: 50% by weight
Starch syrup: 33% by weight
Citric acid: 14% by weight
Flavor material: 1% by weight
Each extract: 0.2% by weight
Water: remaining amount
Sum: 100% by weight

TABLE 2

|  | First Extraction Solvent | Second Extraction Solvent | Macrocarpal Content in Extracts (mg/g) | | |
|---|---|---|---|---|---|
|  |  |  | Macrocarpal A | Macrocarpal B | Macrocarpal C |
| Extract 10 | water | 40% by weight of Ethanol Aqueous Solution | 13.443 | 9.316 | 6.793 |
| Extract 11 |  | 50% by weight of Ethanol Aqueous Solution | 12.349 | 10.347 | 14.779 |
| Extract 12 |  | 60% by weight of Ethanol Aqueous Solution | 14.835 | 11.750 | 21.790 |
| Extract 13 |  | 80% by weight of Ethanol Aqueous Solution | 14.556 | 11.373 | 20.907 |
| Extract 14 |  | 100% by weight of Ethanol | 14.386 | 11.498 | 21.384 |
| Extract 15 | 30% by weight of Ethanol Aqueous Solution | 40% by weight of Ethanol Aqueous Solution | 10.294 | 8.213 | 5.773 |
| Extract 16 |  | 50% by weight of Ethanol Aqueous Solution | 10.799 | 8.367 | 11.279 |
| Extract 17 |  | 80% by weight of Ethanol Aqueous Solution | 11.995 | 9.228 | 18.016 |
| Extract 18 |  | 100% by weight of Ethanol | 11.304 | 9.536 | 18.830 |

Table 2 shows that a high proportion of Macrocarpal A, Macrocarpal B and Macrocarpal C are contained in the Eucalyptus extract prepared by extracting with 0-30% by weight of water or an ethanol aqueous solution in the first extraction solvent, and further extracting with the addition of 50-100% by weight of ethanol aqueous solution or ethanol in the second extraction solvent.

Experimental Example

Using each extraction prepared in the Comparative Example and Example 1 to make samples of a gum and a candy, an evaluation was conducted on processing properties and taste. A Eucalyptus extract was blended in gum such that the concentration of the Eucalyptus extract was about 0.2% by weight, wherein the extract is proven to show an antibacterial activity in the mouth. The results of this Experimental Example are shown in Table 3.

TABLE 3

|  | Coated gum Result | | Candy Result | | |
|---|---|---|---|---|---|
|  | Processing Properties | Taste | Processing Properties | Taste | Product condition |
| Extract 7 | Bad | N/A | Good | Bad | When the required amount was added to the gum, it was in homogeneously distributed. It was highly hygroscopic and low in stability. It was applicable to a candy but left strong bitter and astringent tastes of |

TABLE 3-continued

| | Coated gum Result | | Candy Result | | |
| --- | --- | --- | --- | --- | --- |
| | Processing Properties | Taste | Processing Properties | Taste | Product condition |
| Extract 10 | Bad | N/A | Good | Bad | Eucalyptus with a gritty feeling on the tongue. When the required amount was added to the gum, it was in homogeneously distributed. It was highly hygroscopic and low in stability. It was applicable to a candy but left strong bitter and astringent tastes of Eucalyptus with a gritty feeling on the tongue. |
| Extract 11 | Good | Good | Good | Good | It was possible to add the required amount and there were no bitter and astringent tastes peculiar to Eucalyptus. It could be molded as a gum and also it left a smooth taste on the tongue as a candy. |
| Extract 13 | Good | Good | Good | Good | It was possible to add the required amount and there were no bitter and astringent tastes peculiar to Eucalyptus. It could be molded as a gum and also it left a smooth taste on the tongue as a candy. |
| Extract 14 | Bad | N/A | Bad | N/A | When it was dissolved in aqueous solution, there were some remained apparently insoluble. Homogenous distribution was not possible. |
| Extract 15 | Bad | N/A | Good | Bad | When the required amount was added to the gum, it was in homogeneously distributed. It was highly hygroscopic and low in stability. It was applicable to a candy but left strong bitter and astringent tastes of Eucalyptus with a gritty feeling on the tongue. |
| Extract 16 | Good | Good | Good | Good | It was possible to add the required amount and there were no bitter and astringent tastes peculiar to Eucalyptus. It could be molded as a gum and also it left a smooth taste on the tongue as a candy. |
| Extract 17 | Good | Good | Good | Good | It was possible to add the required amount and there were no bitter and astringent tastes peculiar to Eucalyptus. It could be molded as a gum and also it left a smooth taste on the tongue as a candy. |
| Extract 18 | Bad | N/A | Bad | N/A | When it was dissolved in aqueous solution, there were some remained apparently insoluble. Homogenous distribution was not possible |

GOOD=with respect to processing properties, it is in good condition in molding and the appearance; with respect to taste, it has no bitter, astringent taste specific to Eucalyptus and no gritty feeling on the tongue. BAD=with respect to processing properties, it is the condition in which molding is impossible; with respect to taste, it is the condition in which bitter, astringent taste specific to Eucalyptus cannot be assumed. N/A=Evaluation on taste was impossible because molding was impossible due to poor processing.

In the case of a food whose size is limited, such as a gum, a candy, or a tablet, among others, having an effective ingredient in higher concentration is much more useful.

Based on the results shown in Table 3, it was presumed that the extract prepared by extracting with 0-30% by weight of water or an ethanol aqueous solution in the first extraction solvent, and further extracting with the addition of 50-80% by weight of ethanol aqueous solution in the second extraction solvent contains a high proportion of macrocarpals in the Eucalyptus extract and also enables a decrease in the Eucalyptus specific taste (a bitter or astringent taste) and that it is most suitable for the food, particularly a gum, a candy, and a tablet in view of the processing properties and taste.

Application Example 1

Using Eucalyptus extracts (Extracts 11, 13, 16 and 17) prepared in the method of the Example 1, gums, candies, and tablets were produced using the following methods:

Formula of Gum 1
Xylitol: 45% by weight
Maltitol: 33% by weight
Gum base: 14% by weight
Flavor material: 1% by weight
Extract 11: 0.2% by weight
Others: remaining amount
Sum: 100% by weight Formula of Gum 2
Xylitol: 45% by weight
Maltitol: 33% by weight
Gum base: 14% by weight
Flavor material: 1% by weight
Extract 13: 0.3% by weight
Others: remaining amount
Sum: 100% by weight Formula of Candy 1
Sugar: 50% by weight
Starch syrup: 33% by weight
Citric acid: 14% by weight
Flavor material: 1% by weight
Extract 16: 0.5% by weight
Water: remaining amount
Sum: 100% by weight Formula of Tablet 1
Sugar: 76.1% by weight
Glucose: 19.0% by weight
Sucrose fatty acid ester: 0.2% by weight
Flavor material: 1% by weight
Extract 17: 0.5% by weight
Water: remaining amount
Sum: 100% by weight

INDUSTRIAL APPLICABILITY

According to the method of the present invention, the Eucalyptus extract can be prepared with macrocarpals as a physiologically activity material in higher content than using a conventional method and also can decrease the Eucalyptus specific taste. Accordingly, it is particularly useful for food and beverage whose standard is limited.

Although the present invention has been described in connection with a preferred embodiment, it should be understood that modifications, alterations, and additions can be made to the invention without departing from the scope of the invention as defined by the claims.

What is claimed is:

1. A method for preparing a Eucalyptus extract, the method comprising the steps of:
   (a) removing essential oil form Eucalyptus leaves by steam distillation and drying and pulverizing the leaves to obtain a dried leaf powder;
   (b) extracting said powder with a first solvent, wherein the first solvent is an aqueous solution comprising ethanol at a concentration of less than or equal to 30%;
   (c) filtering the first solvent to obtain an extraction residue,
   (d) heating the extraction residue to reflux at between 20° C. to 100° C. for about 10 minutes to 24 hours in a second solvent, wherein the second solvent is an aqueous solution comprising ethanol at a concentration between 50 to 80%; and
   (e) filtering the second solvent to obtain a filtrate, wherein the filtrate is said Eucalyptus extract, and wherein said Eucalyptus extract comprises Macrocarpal A, Macrocarpal B, and Macrocarpal C in an amount between 3-5% by weight.

2. The method of claim 1, wherein in step (c), the filtering is performed using a solid-liquid separation.

3. The method of claim 1, wherein in step (d), the filtering is performed using a solid-liquid separation.

4. The method of claim 1, further comprising the step of freeze-drying said extract after.

5. The method of claim 1, wherein steps (b) and (d) are performed at a temperature between 20° C. and 100° C.

* * * * *